(12) United States Patent

McInerney et al.

(10) Patent No.: US 12,558,476 B2

(45) Date of Patent: Feb. 24, 2026

(54) INFUSION PUMP ADMINISTRATION SYSTEM

(71) Applicant: CareFusion 303, Inc., San Diego, CA (US)

(72) Inventors: David McInerney, Limerick (IE); Tomasz Cwik, Limerick (IE); Steven Atkinson, Limerick (IE)

(73) Assignee: CareFusion Corporation, San Diego, CA (US)

( * ) Notice: Subject to any disclaimer, the term of this patent is extended or adjusted under 35 U.S.C. 154(b) by 518 days.

(21) Appl. No.: 17/230,736

(22) Filed: Apr. 14, 2021

(65) Prior Publication Data

US 2021/0322670 A1 Oct. 21, 2021

Related U.S. Application Data

(60) Provisional application No. 63/010,610, filed on Apr. 15, 2020.

(51) Int. Cl.
*G16H 20/17* (2018.01)
*A61M 5/142* (2006.01)
*A61M 5/168* (2006.01)

(52) U.S. Cl.
CPC ........ *A61M 5/142* (2013.01); *A61M 5/16877* (2013.01); *G16H 20/17* (2018.01);
(Continued)

(58) Field of Classification Search
CPC .............. A61M 5/142; A61M 5/16877; A61M 2205/18; A61M 2205/52;
(Continued)

(56) References Cited

U.S. PATENT DOCUMENTS 8,777,894 B2 * 7/2014 Butterfield ............. G16H 40/60
604/65
10,226,571 B2 3/2019 Davis et al.
(Continued)

FOREIGN PATENT DOCUMENTS

JP 2006-051244 A 2/2006
JP 2012005756 A * 1/2012 ............. A61M 5/00
WO WO-2014/100687 A2 6/2014

OTHER PUBLICATIONS

JP2012005756A—Suzuki—machine translation (Year: 2012).*
(Continued)

*Primary Examiner* — Jason S Tiedeman

(74) *Attorney, Agent, or Firm* — Mintz Levin Cohn Ferris Glovsky and Popeo, P.C.

(57) ABSTRACT

A method includes receiving, by an infusion pump administration (IPA) device from a first data tag coupled to a fluid storage, a fluid delivery protocol. The fluid delivery protocol includes a fluid parameter associated with the delivery, from a fluid pump, of a fluid from the fluid storage to a patient. The method also includes receiving, by the IPA device from a second data tag coupled to a patient ID, a patient parameter associated with the patient. The method also includes comparing, by the IPA device, the fluid parameter to the patient parameter. The method further includes configuring, by the IPA device, the fluid pump with the fluid parameter and the patient parameter. Related methods and articles of manufacture, including apparatuses and computer program products, are also disclosed.

16 Claims, 8 Drawing Sheets

(52) U.S. Cl.
CPC ..... *A61M 2205/18* (2013.01); *A61M 2205/52* (2013.01); *A61M 2205/583* (2013.01); *A61M 2205/6009* (2013.01)

(58) Field of Classification Search
CPC .... A61M 2205/583; A61M 2205/6009; G16H 20/17; G16H 40/67; G16H 40/63
USPC ........................................ 705/2, 3
See application file for complete search history.

(56) References Cited

U.S. PATENT DOCUMENTS

| | | | | |
|---|---|---|---|---|
| 12,340,888 | B2 * | 6/2025 | Fryman | G16H 40/63 |
| 2002/0038392 | A1 * | 3/2002 | De La Huerga | G16H 20/17 |
| | | | | 710/8 |
| 2003/0009244 | A1 * | 1/2003 | Engleson | G16H 40/40 |
| | | | | 700/86 |
| 2003/0141981 | A1 * | 7/2003 | Bui | A61M 5/142 |
| | | | | 604/500 |
| 2004/0051368 | A1 * | 3/2004 | Caputo | G16H 40/40 |
| | | | | 299/1.9 |
| 2004/0193453 | A1 * | 9/2004 | Butterfield | G16H 40/60 |
| | | | | 977/932 |
| 2006/0047538 | A1 * | 3/2006 | Condurso | G16H 40/67 |
| | | | | 705/3 |
| 2006/0116639 | A1 * | 6/2006 | Russell | G16H 20/17 |
| | | | | 604/131 |
| 2006/0200369 | A1 * | 9/2006 | Batch | G16H 10/60 |
| | | | | 705/3 |
| 2006/0206356 | A1 * | 9/2006 | Vanderveen | G16H 20/17 |
| | | | | 604/103.1 |
| 2006/0229551 | A1 * | 10/2006 | Martinez | G16H 20/17 |
| | | | | 604/67 |
| 2006/0265246 | A1 * | 11/2006 | Hoag | G16H 20/17 |
| | | | | 705/2 |
| 2007/0210157 | A1 * | 9/2007 | Miller | A61B 90/96 |
| | | | | 340/572.1 |
| 2008/0306443 | A1 * | 12/2008 | Neer | A61M 5/007 |
| | | | | 604/121 |
| 2009/0112333 | A1 * | 4/2009 | Sahai | A61M 5/142 |
| | | | | 604/246 |
| 2012/0185267 | A1 * | 7/2012 | Kamen | G16H 20/17 |
| | | | | 705/2 |
| 2013/0102253 | A1 * | 4/2013 | Marsh | H04W 76/15 |
| | | | | 455/41.2 |
| 2013/0197930 | A1 * | 8/2013 | Garibaldi | G16H 20/17 |
| | | | | 705/2 |
| 2013/0274669 | A1 * | 10/2013 | Stempfle | A61M 5/1456 |
| | | | | 604/151 |
| 2014/0067426 | A1 * | 3/2014 | Neff | H04W 4/80 |
| | | | | 705/3 |
| 2015/0001285 | A1 * | 1/2015 | Halbert | G16H 20/17 |
| | | | | 235/375 |
| 2015/0157791 | A1 * | 6/2015 | Desch | G16H 20/17 |
| | | | | 702/50 |
| 2015/0165118 | A1 * | 6/2015 | Lee | A61M 5/14228 |
| | | | | 604/67 |
| 2015/0379237 | A1 * | 12/2015 | Mills | G16H 40/67 |
| 2016/0051750 | A1 * | 2/2016 | Tsoukalis | G16H 40/67 |
| | | | | 235/375 |
| 2016/0114104 | A1 * | 4/2016 | Hyde | A61M 5/16804 |
| | | | | 604/890.1 |
| 2017/0000946 | A1 * | 1/2017 | Boyle | A61M 1/777 |
| 2018/0114598 | A1 * | 4/2018 | Kolberg | G16H 10/60 |
| 2019/0154026 | A1 * | 5/2019 | Kamen | F04B 43/082 |
| 2019/0205578 | A1 * | 7/2019 | Samson | G16H 20/17 |
| 2019/0271681 | A1 * | 9/2019 | McKirdy | G06K 19/0723 |
| 2020/0335195 | A1 * | 10/2020 | Fryman | A61M 5/484 |
| 2021/0308012 | A1 * | 10/2021 | Tagliamento | A61J 3/002 |

OTHER PUBLICATIONS

IBM, System and Method for RFID Usage in the Proper Administration of Medications, IP.com, 4pages (Year: 2008).*
Perez et al., Safety and Traceability in Patient Healthcare through the Integration of RFID Technology for Intravenous Mixtures in the Prescription-Validation-Elaboration-Dispensation-Administration Circuit to Day Hospital Patients, Sensors 2016, 16, 1188, www.mdpi. com/journal/sensors, 24 pages (Year: 2016).*

* cited by examiner

100

130

138

132

132A

130

| Display 132 | Communication Circuitry 134 |
| Data Storage 131 | Controller 136 |
| Alert System 133 | Tag Reader 138 |
| Indicator 135 | |

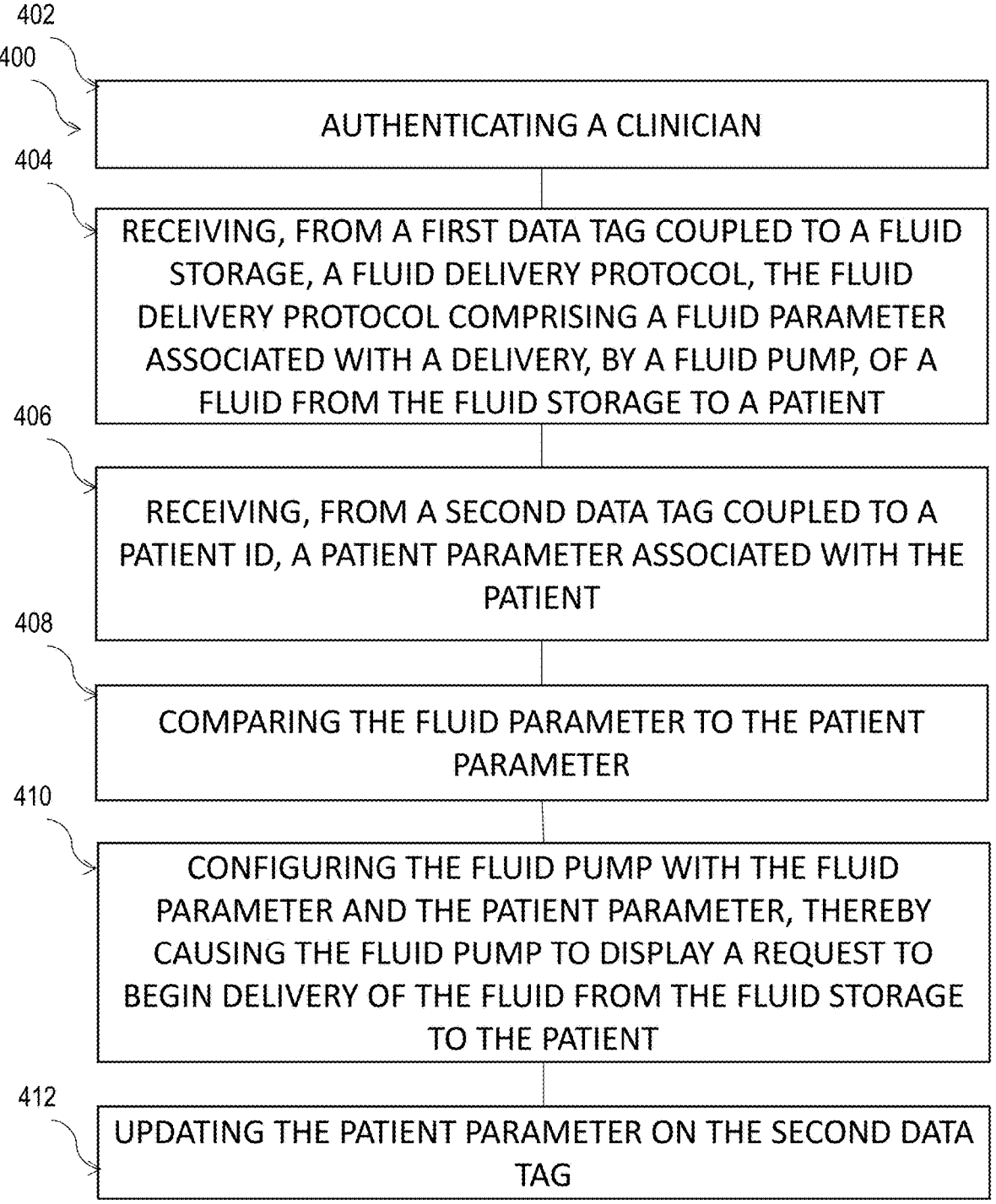

402

400

404

AUTHENTICATING A CLINICIAN

RECEIVING, FROM A FIRST DATA TAG COUPLED TO A FLUID STORAGE, A FLUID DELIVERY PROTOCOL, THE FLUID DELIVERY PROTOCOL COMPRISING A FLUID PARAMETER ASSOCIATED WITH A DELIVERY, BY A FLUID PUMP, OF A FLUID FROM THE FLUID STORAGE TO A PATIENT

406

RECEIVING, FROM A SECOND DATA TAG COUPLED TO A PATIENT ID, A PATIENT PARAMETER ASSOCIATED WITH THE PATIENT

408

COMPARING THE FLUID PARAMETER TO THE PATIENT PARAMETER

410

CONFIGURING THE FLUID PUMP WITH THE FLUID PARAMETER AND THE PATIENT PARAMETER, THEREBY CAUSING THE FLUID PUMP TO DISPLAY A REQUEST TO BEGIN DELIVERY OF THE FLUID FROM THE FLUID STORAGE TO THE PATIENT

412

UPDATING THE PATIENT PARAMETER ON THE SECOND DATA TAG

INFUSION PUMP ADMINISTRATION SYSTEM

CROSS-REFERENCE TO RELATED APPLICATIONS

The present application claims priority to U.S. Provisional Application No. 63/010,610, filed on Apr. 15, 2020, and titled "Infusion Pump Administration System," the entirety of which is incorporated by reference herein.

TECHNICAL FIELD

The subject matter described herein relates generally to the dispensation of medications and more specifically to an infusion pump administration system for the delivery of medication to a patient.

BACKGROUND

Fluid pumps, such as infusion pumps, administer therapy to patients by delivering a medication or other fluid to the patient. To configure the fluid pumps for delivering the fluid to the patient, a clinician may manually enter, into the pumps, certain fluid parameters related to a fluid delivery protocol, and patient parameters relating to the patient. As a result, a great burden is placed on the clinician to enter the correct values of each of the patient parameters and/or fluid parameters, as incorrectly entered values may lead to delivering the incorrect fluid to the patient or an incorrect dose of the fluid to the patient and causing medical complications for the patient. Even in some instances, during which the fluid parameters and/or the patient parameters are wirelessly transmitted to the fluid pumps, the fluid parameters and/or the patient parameters may be susceptible to exposure due to a security breach.

SUMMARY

Systems, methods, and articles of manufacture, including computer program products, are provided for an infusion pump administration system for dispensing a medication to a patient. For example, the system may provide an infusion pump administration device that may extract data, such as a fluid delivery protocol, fluid parameters, patient parameters, and/or clinician parameters from various peripheral devices, such as a fluid storage, a patient ID, and a clinician ID, and use the extracted data to configure a pump to deliver a fluid to a patient, verify the data, and generate one or more alerts.

According to some aspects, a method may include receiving, by an infusion pump administration (IPA) device from a first data tag coupled to a fluid storage, a fluid delivery protocol. The fluid delivery protocol may include a fluid parameter associated with a delivery, from a fluid pump, of a fluid from the fluid storage to a patient. The method may also include receiving, by the IPA device from a second data tag coupled to a patient ID, a patient parameter associated with the patient. The method may also include comparing, by the IPA device, the fluid parameter to the patient parameter. The method may further include configuring, by the IPA device, the fluid pump with the fluid parameter and the patient parameter, thereby causing the fluid pump to display a request to begin delivery of the fluid from the fluid storage to the patient.

In some aspects, the comparing further includes determining, by the IPA device, that the patient parameter does not correspond (e.g., not the same as, differs by a threshold amount, falls outside a range) to the fluid parameter. The comparing may also include detecting, by the IPA device based on the determination, an error. The comparing may also include generating, by the IPA device, an alert indicating the error.

In some aspects, the receiving the fluid delivery protocol includes scanning, by the IPA device, the first data tag. The receiving may also include storing, by the IPA device, the fluid parameter.

In some aspects, the fluid parameter includes one or more of a fluid type, a rate of fluid delivery, a start time for delivering the fluid, a volume of the fluid to be delivered, a frequency for delivering the fluid, a name of the patient, and a patient ID.

In some aspects, the receiving the patient parameter includes scanning, by the IPA device, the second data tag. The receiving may also include storing, by the IPA device, the patient parameter.

In some aspects, the patient parameter includes one or more of a fluid type, a rate of fluid delivery, a start time for delivering the fluid, a volume of the fluid to be delivered, a frequency for delivering the fluid, a name of the patient, and previous infusion information.

In some aspects, the configuring the fluid pump includes scanning, by the IPA device, a third data tag coupled to the fluid pump. The configuring may also include writing, by the IPA device, the fluid parameter and the patient parameter, to the third data tag.

In some aspects, the method also includes authenticating, by the IPA device, a clinician, to provide access to the IPA device. The authenticating may include scanning, by the IPA device, a third data tag coupled to a clinician ID.

In some aspects, the method includes updating, by the IPA device, the patient parameter on the second data tag. The updating may include scanning, by the IPA device, the second data tag coupled to the patient ID. The updating may also include writing, by the IPA device, an updated patient parameter, to the second data tag.

In some aspects, the comparing further includes determining that the patient parameter is the same as the fluid parameter.

In some aspects, the IPA device may be held by a user.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, a peer-to-peer mesh network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an infusion pump administration system, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 4 depicts a flowchart illustrating a process for configuring an infusion pump, in accordance with some example embodiments;

When practical, similar reference numbers denote similar structures, features, or elements.

DETAILED DESCRIPTION

Figure 1:
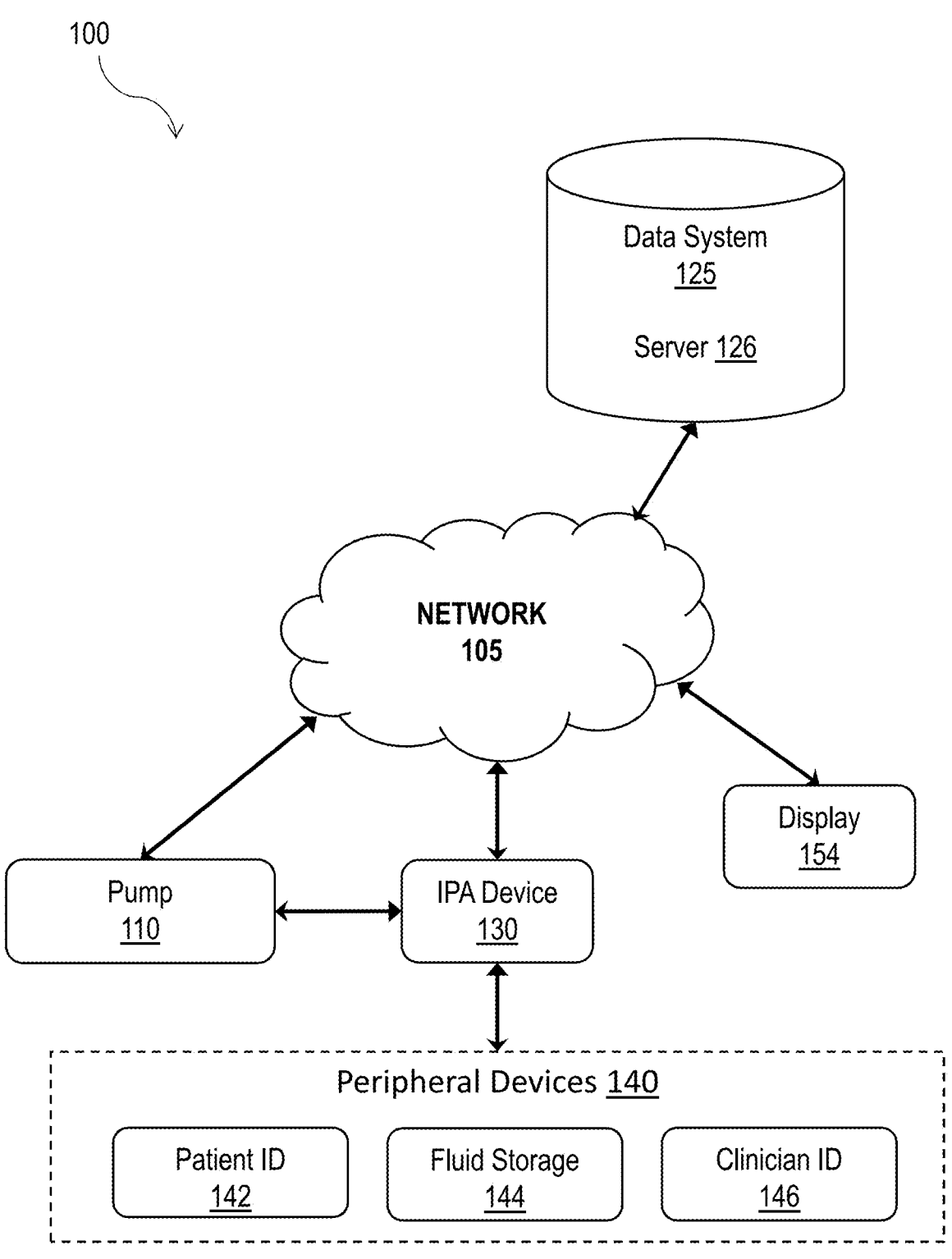
FIG. 1 depicts a system diagram illustrating an infusion pump administration system, in accordance with some example embodiments.

Fluid pumps, such as infusion pumps, administer therapy to patients by delivering a medication or other fluid to the patient. When configuring the fluid pumps to deliver the fluid to the patient, a clinician may generally follow the five rights of medication administration (e.g., the right patient, the right drug, the right dose, the right route, and the right time). For example, a clinician may manually enter, into the pumps, certain fluid parameters related to a fluid delivery protocol and certain patient parameters related to the patient receiving the fluid. The clinician may then manually verify the accuracy of the entered parameters. The fluid parameters, may include a type or a name of a fluid to be delivered to a patient, a rate of fluid delivery, a start and end time for delivering the fluid, a volume of the fluid to be delivered, a frequency for delivering the fluid, and/or the like. The patient parameters may include patient's name, age, height, weight, gender, allergies, prior fluid deliveries, and/or the like. Thus, a large number of fluid-specific and patient-specific parameters may be entered by the clinician into the fluid pumps before the fluid is administered to the patient. This places a great burden on the clinician to enter the correct values of each of the fluid parameters and the patient parameters.

For example, incorrectly entered values of the one or more of the patient parameters or the fluid parameters may lead to significant medical issues, as the infusion pump will deliver the incorrect fluid to the patient, a dose of the fluid to the patient that is too high or too low, and/or a dose of the fluid at the incorrect rate. This situation is likely to be even more prevalent in emergency situations, when the clinician is distracted, rushed, and/or is otherwise not focused on entering the correct values of the patient parameters and/or the fluid parameters and following the five rights of medication administration. In such circumstances, it is also even more important for the correct values of each of the parameters to be entered into the pump. Errors made in the entry of the value of each of the patient parameters and/or the fluid parameters may be compounded when errors are made in more than one patient parameter and/or more than one fluid parameter, thereby furthering the damage to the patient caused by the clinician's error.

Consistent with implementations of the current subject matter, the infusion pump administration system described herein may include a pump administration device that extracts the patient parameters and/or the fluid parameters from one or more peripheral devices (e.g., by scanning a data tag coupled to the peripheral devices), verifies that the extracted parameters are correct, and configures an infusion pump with the extracted parameters. This helps to reduce the burden on the clinician, as the clinician would not need to manually enter the values of the patient parameters and/or the fluid parameters into the infusion pump. Instead, the clinician may begin the delivery of fluid to the patient without physically entering the values of the parameters into the fluid pumps and/or without the clinician needing to verify the accuracy of the entered values. The infusion pump administration device described herein may also allow for easier verification of the five rights of medication administration, as the infusion pump administration device may compare at least one of the patient parameters with at least one of the fluid parameters to verify that the delivery of the fluid to the patient includes the right patient, the right drug, the right dose, the right route, and/or the right time.

Additionally and/or alternatively, the infusion pump administration device described herein may help to prevent incorrect dosing of the fluid to be delivered to the patient. The pump administration device may track previous infusions of the fluid to the individual patient. This allows the pump administration device to verify the fluid delivery protocol against one or more prior fluid delivery protocols. For example, the infusion pump administration device may scan a data tag on a patient ID to retrieve information about the patient's previous fluid delivery protocols, and may scan a data tag on a fluid storage to retrieve information about the patient's current fluid delivery protocol. The infusion pump administration device may then compare the retrieved information about the patient's previous and current fluid delivery protocols.

Even in some instances, during which the fluid parameters and/or the patient parameters are wirelessly transmitted to fluid pumps, the fluid parameters and/or the patient parameters may be susceptible to exposure due to a security breach. This is especially troubling, as the fluid parameters and/or the patient parameters may include certain personal data. The infusion pump administration device described herein scans and retrieves the fluid parameters and/or the patient parameters from a data tag positioned on, coupled to, and/or integrally formed with one or more peripheral devices, such as a fluid storage, a patient ID, and/or a clinician ID. In such instances, the infusion pump administration device may retrieve the fluid parameters and/or the patient parameters from the one or more peripheral devices when the infusion pump administration device is positioned within a predetermined distance from the one or more peripheral devices. Similarly, the infusion pump administration device may transmit the retrieved fluid parameters and/or the patient parameters to the fluid pump when the infusion pump administration device is positioned within a predetermined distance from the fluid pump. These configurations help to improve security of the data being transferred between devices and helps to limit or reduce exposure to a security breach. Additionally and/or alternatively, the data being retrieved and/or transmitted may be encrypted to further improve the security of data transfer within the infusion pump administration system.

FIG. 1 depicts a system diagram illustrating an infusion pump administration system 100, in accordance with some example embodiments. Referring to FIG. 1, the infusion pump administration system 100 may include a pump 110, an infusion pump administration (IPA) device 130, one or more peripheral devices 140, a display 154, and a data system 125. The pump 110, the IPA device 130, the display 154, and/or the data system 125 may be communicatively coupled to one another via a network 105 and/or via a direct device-device connection as described herein. The network 105 may be a wired and/or wireless network including, for example, a public land mobile network (PLMN), a local area network (LAN), a virtual local area network (VLAN), a wide area network (WAN), the Internet, a short range radio connection, for example Bluetooth, a peer-to-peer mesh network, and/or the like.

The display 154 may form a part of the pump 110, the IPA device 130, and/or one or more peripheral devices 140. The display 154 may also include a user interface. The user interface may form a part of a display screen of the display 154 that presents information to a user (e.g., a clinician, a patient, or caregiver for the patient) and/or the user interface may be separate from the display screen. For example, the user interface may be one or more buttons, or portions of the display screen that is configured to receive an entry from the user.

The data system 125 may include one or more databases, providing physical data storage within a dedicated facility and/or being locally stored on the pump 110. The data system 125 may include an inventory system, a patient care system, an administrative system, an electronic medical record system, and/or the like, which store a plurality of electronic medical records, each of which include the patient's medical history, one or more patient parameters, one or more fluid delivery protocols (including one or more fluid parameters), and/or the like. Additionally and/or alternatively, the data system 125 may include cloud-based systems providing remote storage of data in, for example, a multi-tenant computing environment and/or the like. The data system 125 may also include non-transitory computer readable media.

The data system 125 may include and/or be coupled to a server 126, which may be a server coupled to a network, a cloud server, and/or the like. The IPA device 130 and/or the pump 110 may wirelessly communicate with the server 126. The server 126, which may include a cloud-based server, may provide and/or receive data and/or instructions from the data system 125 to the pump 110 and/or the IPA device 130, to implement one or more features of the fluid therapy protocols consistent with embodiments of the current subject matter. Additionally and/or alternatively, the server 126 may receive data (e.g., one or more fluid therapy parameters and/or one or more patient parameters) from the IPA device 130 and/or the pump 110.

The pump 110 may include one or more pumps 110. For example, the pump 110 may include one, two, three, four, five, ten, fifteen, twenty, twenty-five, thirty, or more pumps 110. Moreover, the pump 110 may be part of a patient care system that includes one or more additional pumps. The pump 110 may be a target controlled infusion (TCI) pump, a syringe pump, an anesthesia delivery pump, a patient-controlled analgesic (PCA) pump, a large volume pump (LVP), a small volume pump (SVP), and/or the like, configured to deliver a fluid (e.g., a medication) to a patient. However, it should be appreciated that the pump 110 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Alternatively, the pump 110 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like.

Figure 3A:
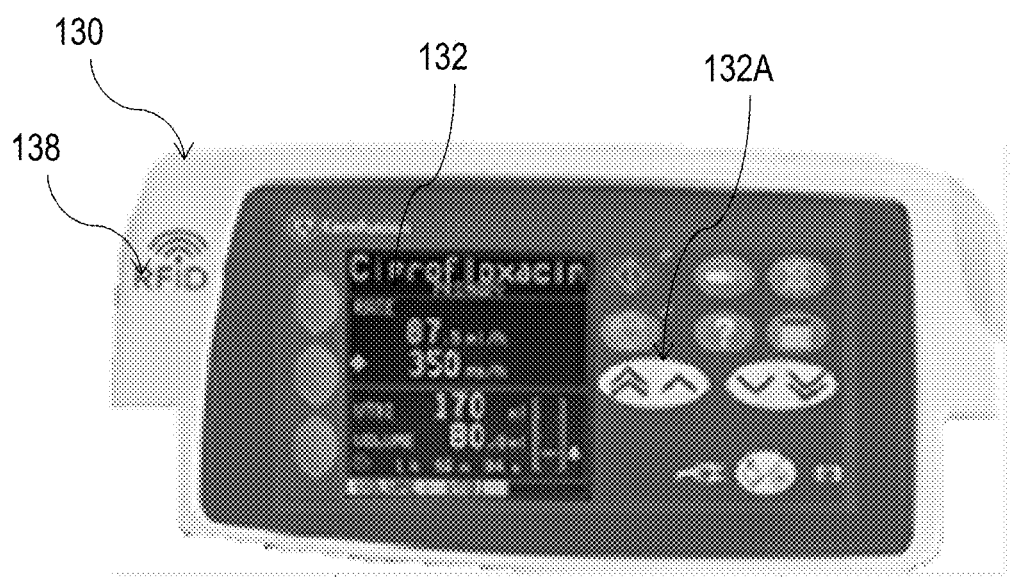
FIG. 3A depicts an infusion pump administration device, in accordance with some example embodiments.
Figure 3B:
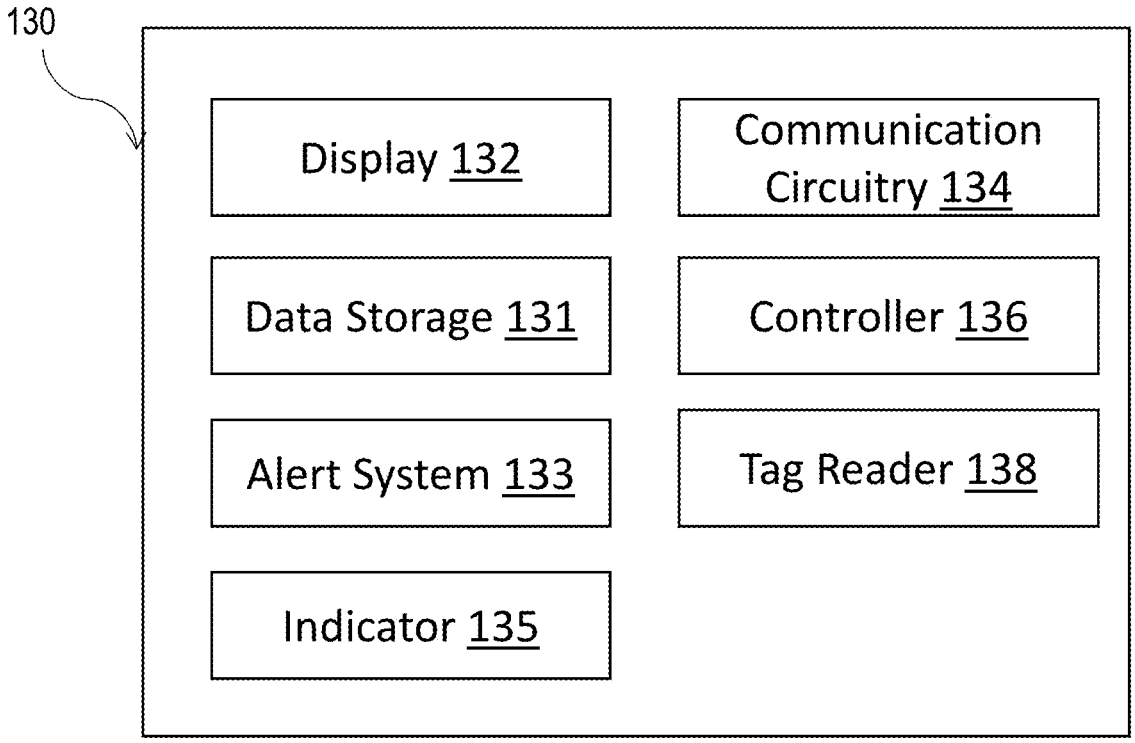
FIG. 3B schematically depicts an infusion pump administration device, in accordance with some example embodiments.

The IPA device 130 may extract one or more patient parameters, clinician parameters, and/or fluid parameters from the one or more peripheral devices 140, verify that the extracted parameters are correct, configure the pump 110 with the extracted parameters, and/or update the parameters stored on the one or more peripheral devices 140. FIG. 3A illustrates an example of the IPA device 130, consistent with embodiments of the current subject matter. FIG. 3B schematically depicts the IPA device 130, consistent with embodiments of the current subject matter. The IPA device 130 may include wireless communication circuitry 134 that is connected to and/or controlled by a controller 136. The wireless communication circuitry 134 may include a tag reader 138, such as a near-field communication (NFC) antenna, a barcode reader, and/or a radio frequency identification (RFID) tag reader, that is configured to read from and/or write to a data tag positioned on or otherwise coupled to the one or more peripheral devices 140 and/or the pump 110. The wireless communication circuitry 134 may include additional components/circuitry for other communication modes, such as, for example, Bluetooth, Bluetooth Low Energy, and/or Wi-Fi chips and associated circuitry (e.g., control circuitry), for communication with other devices. For example, the IPA device 130 may be configured to wirelessly communicate with a remote processor (e.g., the one or more peripheral devices 140, the pump 110, a smartphone, a tablet, wearable electronics, a cloud server, and/or the like) through the wireless communication circuitry 134, and through this communication may receive and/or transmit one or more fluid parameters, one or more patient parameters, one or more clinician parameters, and/or the like from and/or to one or more of the remote processors.

In some embodiments, the IPA device 130 includes a data storage 131, including one or more databases, data tables, and/or the like, for storing (e.g., temporarily storing) the one or more fluid parameters, one or more patient parameters, and/or one or more clinician parameters. As described in more detail below, the controller 136 of the IPA device 130 may verify the one or more fluid parameters, one or more patient parameters, and/or one or more clinician parameters, such as a type of fluid to be delivered, a dosage of the fluid to be delivered, a delivery rate of the fluid to be delivered, a delivery rate of the fluid to be delivered, and/or the like. For example, the controller 136 may compare one or more of the stored fluid parameters to one or more of the patient parameters to determine whether the stored fluid parameters is the same as the stored patient parameters. In some embodiments, the IPA device 130 includes an alert system 133, which generates an audio (e.g., a sound, a patterned sound, and/or the like) and/or visual (e.g., a light, a flashing light, a colored light, a patterned light, and/or the like) alert via an indicator 135 on the IPA device 130, such as when the controller 136 determines that the compared fluid parameter is does not correspond to (e.g., differs from) the patient parameter.

Referring to FIGS. 3A and 3B, the IPA device 130 may be a handheld device that is carried by the user. The IPA device 130 may include a handheld body that has a size, shape, and/or weight that can be easily gripped, moved, and/or held by the user. For example, the handheld body may include a width that fits within a hand of a user. In some implementations, the handheld body includes a width that can be gripped by one or both hands of a user. In some implementations, the width is approximately 1.0 cm to 2.5 cm, 2.5 to 5.0 cm, 5.0 cm to 7.5 cm, 7.5 cm to 10.0 cm, 10.0 cm to 12.5 cm, 12.5 cm to 15.0 cm, 15.0 cm to 17.5 cm, 17.5 cm to 20.0 cm, 2.5 cm to 10.0 cm, and/or other ranges therebetween. In some implementations, the handheld device is a mobile device. The IPA device 130 includes a display 132, which may present to the user one or more of the stored patient parameters, clinician parameters, and/or fluid parameters. The display 132 may include or be a part of a user interface of the IPA device 130. For example, the IPA device 130 may include one or more buttons 132A, which may be selected by the clinician to select or change presented parameters, and/or perform various functions with the IPA device 130. In some embodiments, the IPA device 130 reads from and/or writes to a data tag of the one or more peripheral devices 140 and/or the pump when the IPA device 130 is positioned away from the data tag within a predetermined distance and/or for a predetermined amount of time. The predetermined distance may be approximately 3 cm. In some embodiments, the predetermined distance is approximately 1 to 2 cm, 2 to 3 cm, 3 to 4 cm, and/or other ranges therebetween. In other embodiments, the IPA device 130 may be held in contact with the data tag. The predetermined amount of time may be 0.5 seconds to 1 second. In some embodiments, the predetermined amount of time is approximately less than 0.1 seconds, 0.1 to 0.5 seconds, 0.5 to 1.5 seconds, 1.0 to 2.0 seconds, 2.0 seconds to 3.0 seconds, 3.0 seconds to 4.0 seconds, and/or the like. Thus, the IPA device 130 helps to improve security by reducing or eliminating the likelihood of a security breach.

The one or more peripheral devices 140 may include a patient ID 142, a fluid storage 144, and a clinician ID 146. The patient ID 142 may include a patient ID badge, a patient wristband, and/or the like. The fluid storage 144 may include a fluid delivery bag that is configured to store a fluid and be coupled with the patient via a fluid delivery line. In some embodiments, the fluid storage 144 may additionally and/or alternatively include a syringe configured to deliver the fluid to the patient. The clinician ID 146 may include a clinician ID badge, and the like. A tag, such as a data tag, a near-field communication (NFC) tag, a radio frequency identification (RFID) tag, or other type of wireless transceiver or communication tag, may be positioned on, be integrally formed with, and/or be coupled to at least a portion of one or more of the peripheral devices 140. The data tag may be a type of wireless transceiver and may include a microcontroller unit (MCU), a memory, and an antenna (e.g., an NFC antenna) to perform the various functionalities described herein. The data tag may be, for example, a 1 Kbit or a 2 Kbit NFC tag. NFC tags with other specifications may also be used. The data tag may transmit, receive, and/or store relevant information about each respective peripheral device and/or the parameters relating to each peripheral device 140.

In some embodiments, the patient ID 142 includes a patient ID tag 143 positioned on or otherwise coupled to the patient ID. The patient ID tag 143 may be configured to store, receive, and/or transmit one or more patient parameters, including a patient name, a patient age, a patient height, a patient weight, a patient gender, a patient's allergies, prior fluid delivery information (e.g., a time of fluid delivery, a type of fluid delivered, a rate of fluid delivered, a volume of a fluid delivered, and/or the like), and/or the like. The fluid storage 144 includes a fluid storage tag 145 positioned on or otherwise coupled to the fluid storage 144. The fluid storage tag 145 may be configured to store, receive, and/or transmit one or more fluid delivered parameters, which may be associated with a fluid delivery protocol, including a type or a name of a fluid to be delivered to a patient, a rate of fluid delivery, a start and end time for delivering the fluid, a volume of the fluid to be delivered, a frequency for delivering the fluid, a name of a patient for which the fluid was prepared, and/or the like. The clinician ID 146 includes a clinician ID tag 147 positioned on or otherwise coupled to the clinician ID 146. The clinician ID tag 147 may be configured to store, receive, and/or transmit one or more clinician parameters, including the clinician's name and a history of the clinician's prior scans, such as a time of a prior scan for the patient, a fluid previously scanned by the clinician, a count of prior scans for the patient and/or the type of fluid, and/or the like. As described herein, the one or more patient parameters, fluid parameters, and/or clinician parameters may include values of each of the patient parameters, fluid parameters, and/or clinician parameters, respectively.

Additionally and/or alternatively, the pump 110 may include a pump tag 149. The pump tag 149 may be positioned on and/or otherwise be coupled to the pump 110. The pump tag 149 may be configured to store, receive, and/or transmit the one or more patient parameters, the one or more fluid parameters, and the one or more clinician parameters. In some embodiments, the IPA device 130 communicates with (e.g., scans, retrieves from, and/or transmits to) the pump tag 149 to receive and/or transmit the one or more patient parameters, the one or more fluid parameters, and the one or more clinician parameters from the one or more peripheral devices 140. Thus, the IPA device 130 acts as a unitary interface between the one or more peripheral devices 140 and the pump 110. In some embodiments, the IPA device 130 communicates with the pump 110 via other communications features, such as via a hard-wired and/or a wireless connection.

In some embodiments, the data tags of the peripheral devices 140 (e.g., the patient ID tag 143, the fluid storage tag 145, and/or the clinician ID tag 147) and/or the data tag of the pump 110 (e.g., the pump tag 149) may allow for secure communication between the IPA device 130 and the peripheral devices 140 and/or the pump 110. For example, the data transferred to and/or from the IPA device 130 may be encrypted using an encryption key. In this example, an encryption key may be stored on the one or more peripheral devices 140, the pump 110, the IPA device 130 and/or the data tags of each of the one or more peripheral devices 140, the pump 110, and/or the IPA device 130 to decrypt encrypted data received by each of the one or more peripheral devices 140 and/or the IPA device 130. In some examples, a data tag, such as the data tags described herein may program the IPA device 130, the peripheral devices 140 and/or the pump 110 with an encryption key. Encrypting the data helps to more securely transfer data between the IPA device 130 and the pump 110 and/or the one or more peripheral devices 140.

Figure 2:
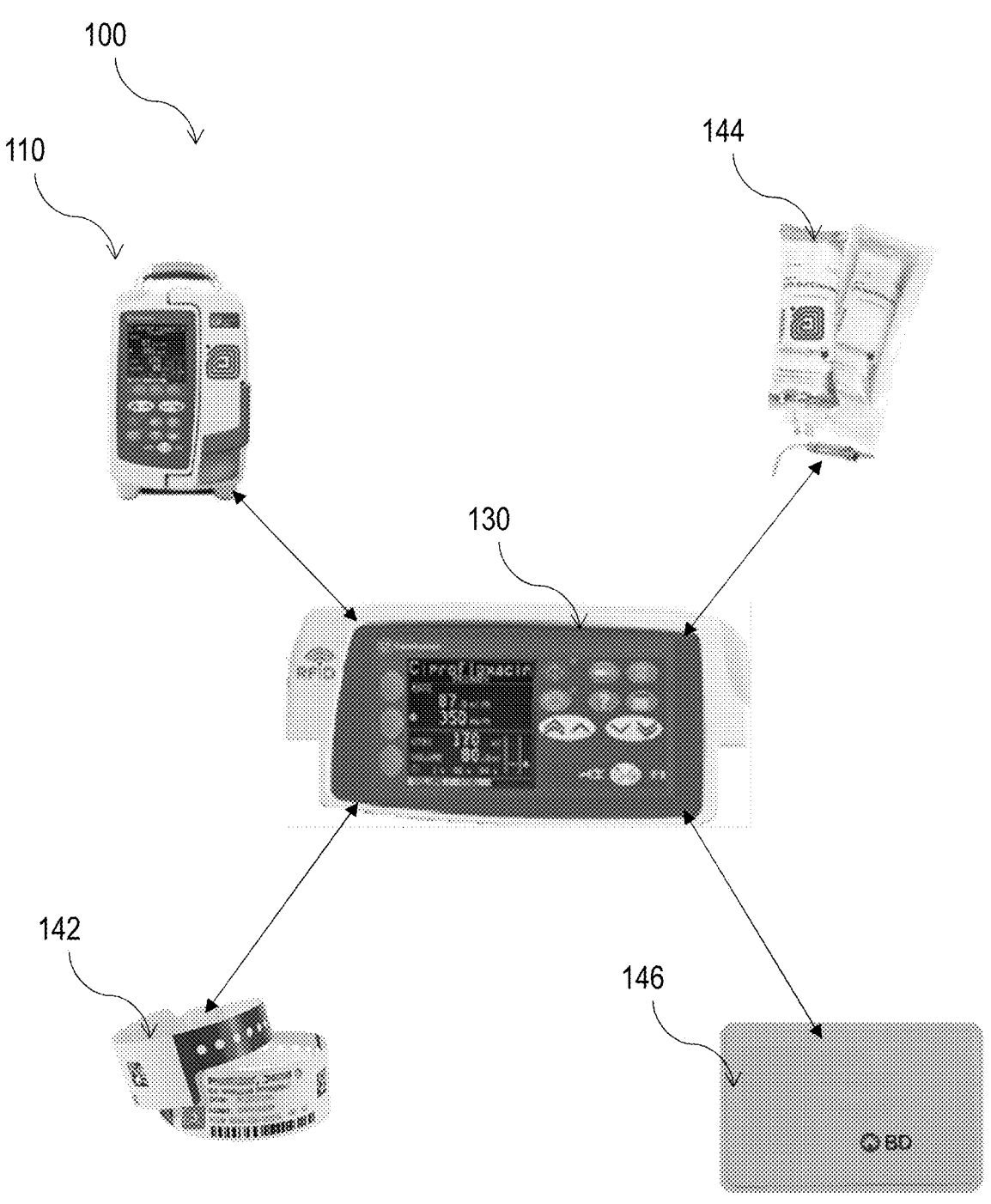
FIG. 2 schematically depicts an infusion pump administration system, in accordance with some example embodiments.

FIG. 2 schematically illustrates an example of the infusion pump administration system 100. The infusion pump administration system 100 includes the IPA device 130, the pump 110, the fluid storage 144, the clinician ID 146, and the patient ID 142. As noted above, the IPA device 130 may communicate with the fluid storage 144, the clinician ID 146, and the patient ID 142 to retrieve one or more patient parameters, clinician parameters, and/or fluid parameters, verify the extracted parameters, configure the pump 110 with the retrieved parameters, and/or update the parameters stored on the fluid storage 144, the clinician ID 146, and the patient ID 142. This helps to limit or prevent errors in configuring a pump for delivering a fluid to the patient. As a result, the IPA device 130 helps to decrease or eliminate the likelihood that the incorrect dose and/or type of fluid is delivered to the patient.

As noted above, the one or more peripheral devices 140 including the patient ID 142, the fluid storage 144, and the clinician ID 146 may include a data tag, such as the patient ID tag 143, the fluid storage tag 145, and the clinician ID tag 147. In some embodiments, the patient ID 142 may be prepared, such as when the patient checks into a medical facility or before the patient begins or continues a treatment involving the delivery of fluid to the patient. To prepare the patient ID 142, the one or more patient parameters (e.g., a patient name, a patient age, a patient height, a patient weight, a patient gender, a patient's allergies, prior fluid delivery information, and/or the like) may be written to the patient ID tag 143 that is positioned on and/or coupled to the patient ID 142. Before or after the patient parameters are written to the patient ID tag 143, the values of the patient parameters may be encrypted to improve the security of the stored data. In some embodiments, when the fluid storage 144 is prepared, a fluid delivery protocol including the one or more fluid parameters (e.g., a type or a name of a fluid to be delivered to a patient, a rate of fluid delivery, a start and end time for delivering the fluid, a volume of the fluid to be delivered, a frequency for delivering the fluid, a name of a patient for which the fluid was prepared, and/or the like), is written to the fluid storage tag 145. Before or after the fluid parameters are written to the fluid storage tag 145, the values of the fluid parameters may be encrypted to improve the security of the stored data. In some embodiments, the clinician parameters may be written to the clinician ID tag 147 of the clinician ID 146 (e.g., at the time of the clinician taking a position). Before or after the clinician parameters are written to the clinician ID tag 147, the values of the clinician parameters may be encrypted to improve the security of the stored data. The one or more patient parameters, the one or more fluid parameters, and/or the one or more clinician parameters may be retrieved from the data system 125 (e.g., the server 126) and written onto the respective peripheral devices 140.

The IPA device 130 (e.g., the controller 136) may be used to extract the one or more patient parameters, the one or more fluid parameters, and/or the one or more clinician parameters from at least one of the peripheral devices 140. In some embodiments, the IPA device 130 may scan the clinician ID 146 (e.g., the clinician ID tag 147), scan the patient ID 142 (e.g., the patient ID tag 143), and scan the fluid storage 144 (e.g., the fluid storage tag 145) before transmitting the one or more patient parameters, the one or more fluid parameters, and/or the one or more clinician parameters to the pump 110. It should be appreciated that the IPA device 130 may scan the peripheral devices 140 in any order before transmitting the one or more patient parameters, the one or more fluid parameters, and/or the one or more clinician parameters to the pump 110. In some embodiments, the IPA device 130 transmits the one or more patient parameters, the one or more fluid parameters, and/or the one or more clinician parameters to the pump 110 after all of the peripheral devices 140 have been read, after reading each of the peripheral devices 140 and/or after any reading any combination of the peripheral devices 140.

To access the IPA device 130, the IPA device 130 may prompt, such as via the user interface of the IPA device 130, the clinician to enter a user name and password, scan a badge, such as the clinician ID 146, perform a fingerprint scan or a retina scan, and/or use facial recognition to identify the clinician. In some embodiments, to authenticate the clinician and/or after the IPA device authenticates the clinician, the IPA device 130 may scan the clinician ID 146. For example, the IPA device 130 may scan, via the tag reader of the IPA device 130, the clinician ID tag 147 to obtain the clinician parameters. In some embodiments, the tag reader of the IPA device 130 scans the clinician ID tag 147 when the IPA device 130 is positioned from the clinician ID 146 (e.g., the clinician ID tag 147) by a predetermined distance and/or for a predetermined amount of time.

The IPA device 130 may store (e.g., temporarily store) the clinician parameters in a database and/or as data objects in memory (e.g., electrically erasable programmable read-only memory) on the IPA device 130 when the IPA device 130 reads the clinician ID tag 147 and receives the clinician parameters from the clinician ID tag 147. After the clinician ID tag 147 is scanned by the IPA device 130, the IPA device 130 may allow for one or more additional peripheral devices 140 to be scanned. In some embodiments, the IPA device 130 displays a prompt, via the display 132 of the IPA device 130, to scan the next peripheral device, such as the fluid storage 144 and/or the patient ID 142.

Additionally and/or alternatively, the IPA device 130 may scan the fluid storage 144. For example, the IPA device 130 may scan, via the tag reader of the IPA device 130, the fluid storage tag 145 to obtain the fluid parameters. In some embodiments, the tag reader of the IPA device 130 scans the fluid storage tag 145 when the IPA device 130 is positioned from the fluid storage 144 (e.g., the fluid storage tag 145) by a predetermined distance and/or for a predetermined amount of time. The IPA device 130 may store (e.g., temporarily store) the fluid storage parameters in the database on the IPA device 130 when the IPA device 130 reads the fluid storage tag 145 and receives the fluid parameters from the fluid storage tag 145. After the fluid storage tag 145 is scanned by the IPA device 130, the IPA device 130 may allow for one or more additional peripheral devices 140 to be scanned. In some embodiments, the IPA device 130 displays a prompt, via the display 132 of the IPA device 130, to scan the next peripheral device, such as the clinician ID 146 and/or the patient ID 142.

Additionally and/or alternatively, the IPA device 130 may scan the patient ID 142. For example, the IPA device 130 may scan, via the tag reader of the IPA device 130, the patient ID tag 143 to obtain the patient parameters. In some embodiments, the tag reader of the IPA device 130 scans the patient ID tag 143 when the IPA device 130 is positioned from the patient ID 142 (e.g., the patient ID tag 143) by a predetermined distance and/or for a predetermined amount of time. The IPA device 130 may store (e.g., temporarily store) the fluid storage parameters in the database on the IPA device 130 when the IPA device 130 reads the patient ID tag 143 and receives the patient parameters from the patient ID tag 143. After the patient ID tag 143 is scanned by the IPA device 130, the IPA device 130 may allow for one or more additional peripheral devices 140 to be scanned. In some embodiments, the IPA device 130 displays a prompt, via the display 132 of the IPA device 130, to scan the next peripheral device, such as the clinician ID 146 and/or the fluid storage 144.

In some embodiments, after each of the peripheral devices 140 is scanned by the IPA device 130 and/or after a subset (e.g., two, three, or more) of the peripheral devices 140 is scanned by the IPA device 130, the IPA device 130 (e.g., the controller 136) may verify the read and stored parameters by at least comparing one or more related parameters. In some embodiments, two or more parameters may be related when each of the parameters has a same name, category, and/or identifier. As an example, the IPA device 130 may read the fluid storage tag 145 and the patient ID tag 147, and store the fluid parameters and the patient parameters in the database on the IPA device 130. The IPA device 130 may then compare one or more of the fluid parameters with one or more related patient parameters to determine whether the particular fluid parameters match the patient parameters. For example, the IPA device 130 may compare the type of drug stored in the fluid storage of the one or more fluid parameters with the type of drug to be delivered to the patient and/or the patient's allergies of the one or more patient parameters. As another example, the IPA device 130 may compare the name of the patient of the one or more fluid parameters with the name of the patient of the one or more patient parameters. As another example, the IPA device 130 may compare the fluid delivery protocol to be delivered or at least one aspect of the fluid delivery protocol (e.g., a type or a name of a fluid to be delivered to a patient, a rate of fluid delivery, a start and end time for delivering the fluid, a volume of the fluid to be delivered, a frequency for delivering the fluid, a name of a patient for which the fluid was prepared, and the like) to be delivered of the one or more fluid parameters with the fluid delivery protocol to be received or at least one aspect of the fluid delivery protocol (e.g., a type or a name of a fluid to be delivered to a patient, a rate of fluid delivery, a start and end time for delivering the fluid, a volume of the fluid to be delivered, a frequency for delivering the fluid, a name of a patient for which the fluid was prepared, and the like) of the one or more patient parameters. In some embodiments, the IPA device 130 compares the related parameters after scanning at least two peripheral devices 140. Additionally and/or alternatively, the IPA device 130 compares the related parameters after receiving a request, via the user interface of the IPA device 130, to verify the read and stored parameters.

In some embodiments, the IPA device 130 (e.g., the controller 136) may detect an error. For example, the IPA device 130 may detect an error in the retrieved parameters when the IPA device 130 detects that values of at least two related parameters of the read and/or stored parameters do not match or are otherwise not equal. An error may indicate that the fluid stored in the fluid storage 144 is not the correct type of fluid to be delivered to the particular patient or that the fluid delivery protocol (or one or more aspects of the fluid delivery protocol) is incorrect for the particular patient. When the IPA device 130 detects an error, the alert system

133 of the IPA device 130 may generate an audio (e.g., a sound, a patterned sound, and/or the like) and/or visual (e.g., a light, a flashing light, a colored light, a patterned light, and/or the like) alert via an indicator 135 on the IPA device 130. Additionally and/or alternatively, when the IPA device 130 detects an error, the IPA device 130 displays a prompt, via the display of the IPA device 130, for the clinician to correct the error, such as by changing the fluid storage 144 connected to the patient, updating the fluid delivery protocol, and/or changing one or more values on the IPA device 130 by entering, via the user interface of the IPA device 130 the correct values of the parameters.

After the IPA device 130 reads and stores the parameters from one or more of the peripheral devices 140 and/or after the IPA device 130 verifies the values of the parameters read and stored on the IPA device 130, the IPA device 130 may configure the pump 110 by transmitting the parameters to the pump 110. For example, the IPA device 130 may scan the pump tag 149 when the IPA device 130 is positioned from the pump 110 (e.g., the pump tag 149) by a predetermined distance and/or for a predetermined amount of time. Scanning the pump tag 149 may cause the IPA device 130 to write one or more of the stored parameters to the pump 110. In some embodiments in which the stored parameters (or values of the stored parameters) are encrypted, the stored parameters are decrypted at the pump 110 using the encryption key, to improve the security of the data being transferred between devices.

The pump 110 may determine that the parameters have been written to the pump tag 149. In some embodiments, the pump 110 may request confirmation, via a user interface of the pump 110, to begin delivering the fluid to the patient from the fluid storage 144. In some embodiments, the pump 110 displays via a display of the pump 110 values of the received parameters. Accordingly, the pump 110 and/or the IPA device 130 helps to ensure that the five rights of medication administration have been followed, without requiring the clinician to manually enter the values of one or more of the fluid parameters, clinician parameters, and/or patient parameters. This reduces or eliminates the likelihood that medical complications occur during the delivery of the fluid to the patient due to an error in the entered values. Such configurations also help to more quickly configure a pump 110 for delivery fluid to a patient.

In some embodiments, after the parameters are written to the pump tag 149 of the pump 110, one or more patient parameters may be updated by rescanning the patient ID 142 and writing the updated values of the one or more patient parameters to the patient ID tag 143. For example, the patient's prior infusions may be updated by rescanning the patient ID 142. In this example, a time of the fluid delivery, a dose of the fluid delivery, and/or the like may be updated by rescanning the patient ID 142.

FIG. 4 illustrates an example process 400 for implementing an infusion pump administration system (e.g., the infusion pump administration system 100) to configure a fluid pump (e.g., the pump 110) with an IPA device (e.g., the IPA device 130). Consistent with embodiments of the current subject matter, the infusion pump administration system may reduce and/or eliminate errors in the values of one or more parameters entered in the pump, improving the reliability of fluid pumps in delivering a fluid to a patient, and reducing medical complications caused by errors in the entered values. The infusion pump administration system may also improve the security of the data transferred between one or more peripheral devices and the fluid pump via the IPA device.

At 402, an infusion pump administration (IPA) device (e.g., the IPA device 130) may authenticate a clinician. Authenticating the clinician may allow the clinician access to one or more features of the IPA device. For example, authenticating the clinician may allow the clinician to access, enter, and/or change data stored on the IPA device. In some embodiments, authenticating the clinician includes requesting, via a user interface of the IPA device, a user name and password, a badge scan, and/or a fingerprint scan or a retina scan, and/or the use of facial recognition to identify the clinician.

Additionally and/or alternatively, authenticating the clinician includes scanning, by the IPA device, a clinician ID (e.g., the clinician ID 142) and/or a data tag (e.g., the clinician ID tag 143) coupled to the clinician ID. For example, the IPA device may read the data tag coupled to the clinician ID, to retrieve and/or store one or more clinician parameters, including the clinician's name and a history of the clinician's prior scans, such as a time of a prior scan for the patient, a fluid previously scanned by the clinician, a count of prior scans for the patient and/or the type of fluid, and/or the like.

At 404, the IPA device may receive, from a first data tag (e.g., the fluid storage tag 145) coupled to a fluid storage (e.g., the fluid storage 144), a fluid delivery protocol. The fluid delivery protocol may include a fluid parameter associated with a delivery, by a fluid pump, of fluid from the fluid storage to a patient. In some embodiments, the fluid parameter may include one, two, three, four, five, or more fluid parameters. For example, the fluid parameter may include one or more of a fluid type, a rate of fluid delivery, a start time for delivering the fluid, a volume of the fluid to be delivered, a frequency for delivering the fluid, and a name of the patient, and/or the like.

In some embodiments, the IPA device may receive the fluid delivery protocol by scanning the first data tag when the IPA device is positioned from the fluid storage (e.g., the fluid storage tag) by a predetermined distance (e.g., 1 to 2 cm, 2 to 3 cm, 3 to 4 cm, and/or other ranges therebetween) and/or for a predetermined amount of time (e.g., 0.5 to 1.5 seconds, 1.0 to 2.0 seconds, 2.0 seconds to 3.0 seconds, 3.0 seconds to 4.0 seconds, and/or the like). The IPA device may store the received fluid delivery protocol including the fluid parameter on the IPA device.

At 406, the IPA device may receive, from a second data tag (e.g., the patient ID tag 143) coupled to a patient ID (e.g., the patient ID 142), a patient parameter associated with the patient. In some embodiments, the patient parameter may include one, two, three, four, five, or more patient parameters. For example, the patient parameter may include one or more of a patient name, a patient age, a patient height, a patient weight, a patient gender, a patient's allergies, prior fluid delivery information (e.g., a time of fluid delivery, a type of fluid delivered, a rate of fluid delivered, a volume of a fluid delivered, and/or the like), a fluid type, a rate of fluid delivery, a start time for delivering the fluid, a volume of the fluid to be delivered, a frequency for delivering the fluid, and/or the like.

In some embodiments, the IPA device may receive the patient parameter by scanning the second data tag when the IPA device is positioned away from the patient ID (e.g., the patient ID tag) by a predetermined distance (e.g., 1 to 2 cm, 2 to 3 cm, 3 to 4 cm, and/or other ranges therebetween) and/or for a predetermined amount of time (e.g., 0.5 to 1.5 seconds, 1.0 to 2.0 seconds, 2.0 seconds to 3.0 seconds, 3.0 seconds to 4.0 seconds, and/or the like). The IPA device may store the received patient parameter on the IPA device.

At 408, the IPA device may compare the fluid parameter to the patient parameter. Comparing the fluid parameter to the patient parameter may help to verify that the received patient parameter and the fluid parameter are accurate. For example, the IPA device may determine whether the fluid parameter and the patient parameter match. In other words, the IPA device may determine whether a value of the fluid parameter is the same as a value of the patient parameter.

In some embodiments, the IPA device compares at least one patient parameter that is related to at least one fluid parameter. The at least one patient parameter is related to the at least one fluid parameter when the at least one patient parameter has the same name, category, and/or identifier as the at least one fluid parameter. The name, category, and/or identifier may be stored in a table of a database on the IPA device and may be received by the IPA device with the fluid parameter and/or the patient parameter.

In some embodiments, the IPA device determines that the patient parameter matches the fluid parameter. In that case, the IPA device may display a prompt to transmit the patient parameter and/or the fluid parameter to the fluid pump. In other embodiments, the IPA device may determine that the patient parameter is does not correspond to the fluid parameter. The IPA device may detect an error when the patient parameter does not correspond to the fluid parameter. The error may indicate that the fluid stored in the fluid storage is not the correct type of fluid to be delivered to the particular patient or that the fluid delivery protocol (or one or more parameters of the fluid delivery protocol) is incorrect for the particular patient. When the IPA device detects an error, the IPA device may generate an audio (e.g., a sound, a patterned sound, and/or the like) and/or visual (e.g., a light, a flashing light, a colored light, a patterned light, and/or the like) alert via an indicator or display of the IPA device. Additionally and/or alternatively, when the IPA device detects an error, the IPA device displays a prompt, via the display of the IPA device, for the clinician to correct the error, such as by disabling power to the pumping mechanism included in the fluid pump, changing the fluid storage connected to the patient, updating the fluid delivery protocol, and/or changing one or more values on the IPA device by entering, via the user interface of the IPA device the correct values of the parameters. An error may also cause an adjustment to one or more physical elements of the IPA device or the fluid pump. For example, the error may disable power to the pumping mechanism included in the fluid pump. As another example, the error may cause adjustment to the communications hardware of the IPA device and/or fluid pump to ensure priority is given to signals transmitted or received between the two devices. For example, the signal strength may be increased to ensure efficient and expedited exchange of error messages along with subsequent messages that may, for instance, remediate the error such as by configuring the fluid pump to operate within acceptable parameters.

At 410, the IPA device may configure the fluid pump with the fluid parameter and the patient parameter. This may cause the fluid pump to display a request to begin delivery of the fluid from the fluid storage to the patient. In some embodiments, the IPA device may configure the fluid pump by scanning a third data tag (e.g., the pump tag 149) coupled to the fluid pump. The IPA device may also write the fluid parameter and/or the patient parameter to the fluid pump (e.g., to the third data tag). As an example, the fluid pump may detect that the fluid parameter and/or the patient parameter have been written to the third data tag. Additionally and/or alternatively, the fluid pump may determine that the IPA device has scanned the fluid pump. Before delivering the fluid to the patient, the fluid pump may present, via the display of the fluid pump, the patient parameter and/or the fluid parameter. The fluid pump may also request a confirmation, via a user interface of the fluid pump, that the parameters are accurate and/or that the fluid pump should deliver the fluid to the patient. In some embodiments, the fluid pump may receive a confirmation or other input, via the user interface of the fluid pump. The fluid pump may then deliver the fluid to the patient. This configuration may provide an additional check to ensure that the displayed fluid parameter and/or the patient parameter are accurate. As a result, the IPA device may cause (e.g., indirectly cause) the fluid pump to deliver the fluid to the patient.

At 412, the IPA device may update the patient parameter on the second data tag. The IPA device may update the patient parameter on the second data tag after the patient and/or fluid parameters are written to the pump tag of the fluid pump. To update the patient parameter on the second data tag, the IPA device may rescan the patient ID and write the updated patient parameter to the patient ID (e.g., the second data tag). For example, the patient's prior infusions may be updated by rescanning the patient ID. In this example, a time of the fluid delivery, a dose of the fluid delivery, and/or the like may be updated by rescanning the patient ID.

Although the process 400 is generally described with respect to the patient parameter and the fluid parameter, the process 400 may be performed with the patient parameter, the fluid parameter, and/or the clinician parameter described herein.

Figure 5:
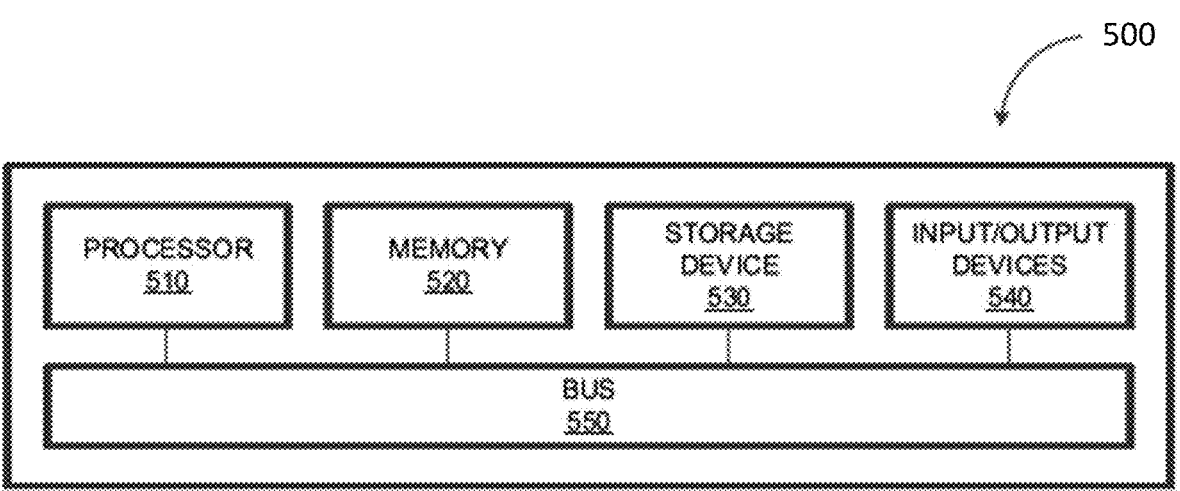
FIG. 5 depicts a block diagram illustrating a computing system, in accordance with some example embodiments.

FIG. 5 depicts a block diagram illustrating a computing system 500 consistent with embodiments of the current subject matter. Referring to FIGS. 1 and 5, the computing system 500 can be used to implement the pump 110, the IPA device 130, the one or more peripheral devices 140, the data systems 125, the server 126, the display 154, and/or any components therein.

As shown in FIG. 5, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the pump 110 and/or the IPA device 130. In some example embodiments, the processor 510 can be a single-threaded processor. Alternatively, the processor 510 can be a multi-threaded processor. The processor 510 is capable of processing instructions stored in the memory 520 and/or on the storage device 530 to present graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device, and/or user interface buttons. In various embodiments, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, embedded display, etc.).

Figure 6A:
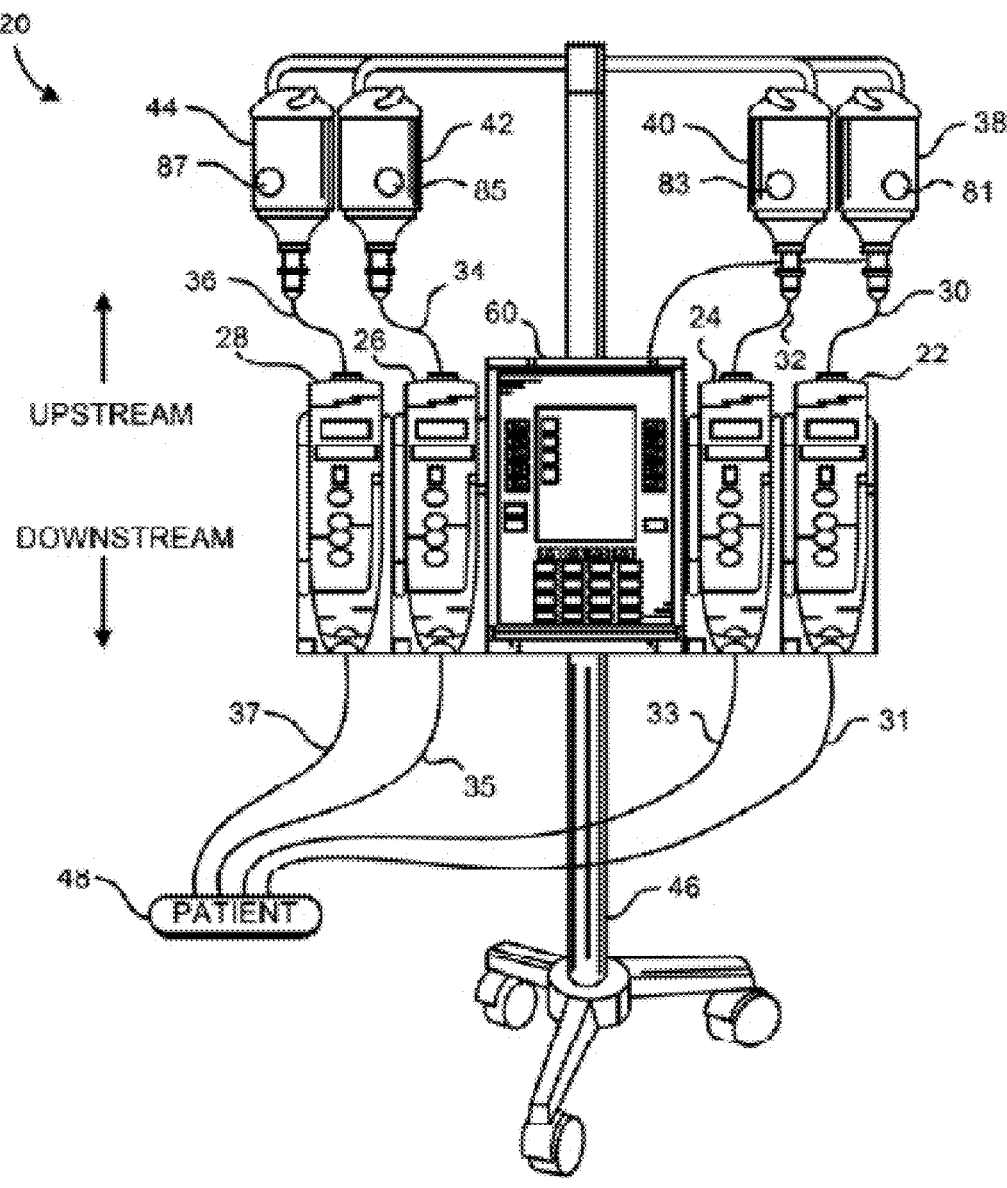
FIG. 6A depicts a front view of a patient care system, in accordance with some example embodiments.
Figure 6B:
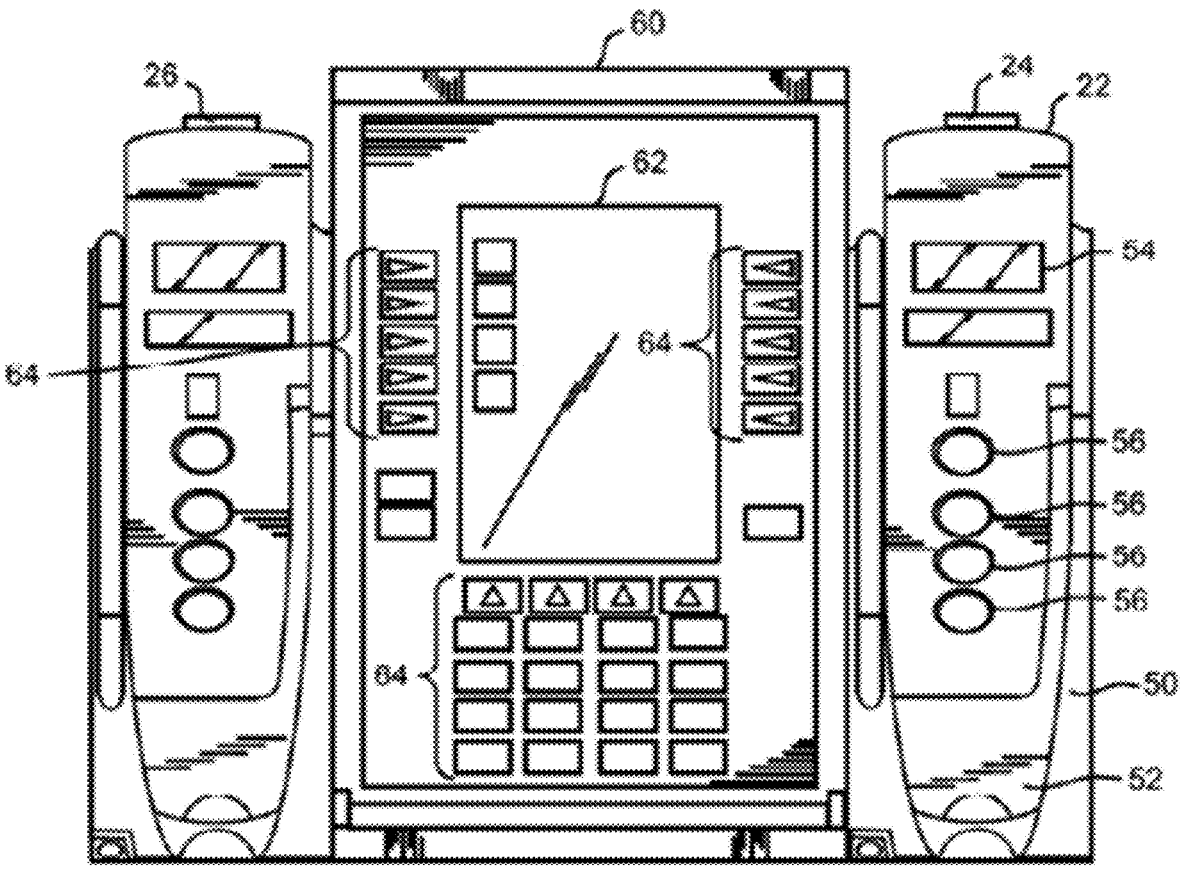
FIG. 6B depicts an enlarged view of a portion of a patient care system, in accordance with some example embodiments.
Figure 6C:
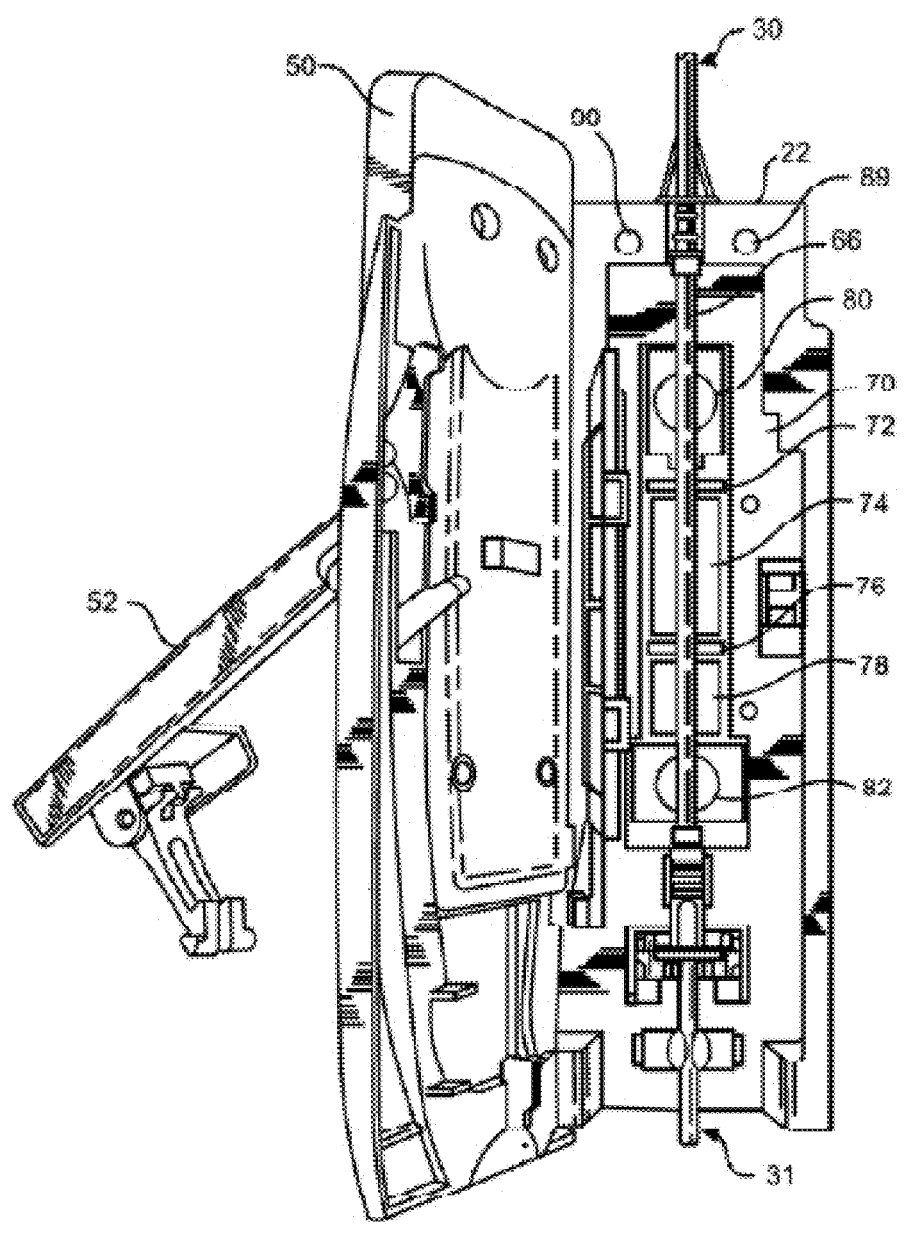
FIG. 6C depicts a perspective view of a pump, in accordance with some example embodiments.

In some example embodiments, a pump 22 (e.g., the pump 110) may be part of a patient care system 20. FIGS. 6A-6C illustrate example embodiments of the patient care system 20, though other types of patient care systems may be implemented. Referring to FIG. 6A, the patient care system 20 may include the pump 22 as well as additional pumps 24, 26, and 28. Although a large volume pump (LVP) is illustrated, other types of pumps may be implemented, such as a small volume pump (SVP), a TCI pump, a syringe pump, an anesthesia delivery pump, and/or a patient-controlled analgesic (PCA) pump configured to deliver a medication to a patient in accordance with one or more fluid delivery protocols. In some embodiments, the pump 110 described herein may be communicatively coupled with and/or form a part of the pumps 22, 24, 26, 28. The pump 22 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like, or the pump 22 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. In some embodiments, the IPA device 130 may be communicatively coupled with the pumps 22, 24, 26, 28. For example, the pumps 22, 24, 26, 28 may each include a data tag. The IPA device 130 may read data from and/or write data to the data tag of each of the pumps 22, 24, 26, 28. In some embodiments, the pumps 22, 24, 26, 28 communicate with the one or more peripheral devices 140 via the IPA device 130.

As shown in FIG. 6A, each of the pump 22, 24, 26, and 28 may be fluidly connected with an upstream fluid line 30, 32, 34, and 36, respectively. Moreover, each of the four pumps 22, 24, 26, and 28 may also fluidly connected with a downstream fluid line 31, 33, 35, and 37, respectively. The fluid lines can be any type of fluid conduit, such as tubing, through which fluid can flow. At least a portion of one or more of the fluid lines may be constructed with a multi-layered configuration as described herein.

Fluid supplies 38, 40, 42, and 44 (e.g., the fluid storage 144), which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 may be mounted to a roller stand or intravenous (IV) pole 46.

A separate pump 22, 24, 26, and 28 may be used to infuse each of the fluids of the fluid supplies into the patient. The pumps 22, 24, 26, and 28 may be flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 6A. Many have check valves, drip chambers, valved ports, connectors, and other devices well known to those skilled in the art. These other devices have not been included in the drawings so as to preserve clarity of illustration. In addition, it should be noted that the drawing of FIG. 6A is not to scale and that distances have been compressed for the purpose of clarity. In an actual setting, the distance between the bottles 38, 40, 42, and 44 and the pump modules 22, 24, 26, and 28 could be much greater.

Referring now to FIG. 6B, an enlarged view of the front of the patient care system 20 is shown. The pump 22 may include a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 6C. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). The display 54 may otherwise be a part of or be coupled to the pump 22. Control keys 56 exist for programming and controlling operations of the pump as desired. The pump 22 also includes audio alarm equipment in the form of a speaker (not shown).

In the embodiment shown, a programming module 60 is attached to the left side of the pump 22. In some embodiments, the programming module 60 forms a part of the pump 22. Other devices or modules, including another pump, may be attached to the right side of the pump 22, as shown in FIG. 6A. In such a system, each attached pump represents a pump channel of the overall patient care system 20. In one embodiment, the programming module is used to provide an interface between the pump 22 and external devices as well as to provide most of the operator interface for the pump 22.

The programming module 60 includes a display 62 for visually communicating various information, such as the operating parameters of the pump 22 and alert indications and alarm messages. In some embodiments, the display 62 forms a part of the pump 110. The programming module 60 may additionally and/or alternatively display the one or more patient parameters, fluid parameters, and/or clinician parameters and the corresponding values for each of the one or more patient parameters described herein to the display 54 and/or the display 64. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. In some embodiments, the programming module includes and/or is coupled to a data tag. The IPA device 130 described herein may read data from and/or write data to the data tag. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump.

The communications system may take the form of a radio frequency ("RF") (radio frequency) system, an optical system such as infrared, a Blue Tooth system, or other wired or wireless system. The bar code scanner and communications system may alternatively be included integrally with the pump 22, such as in cases where a programming module is not used, or in addition to one with the programming module. Further, information input devices need not be hard-wired to medical instruments, information may be transferred through a wireless connection as well.

FIG. 6B includes a second pump 26 connected to the programming module 60. As shown in FIG. 6A, more pump modules may be connected. Additionally, other types of modules may be connected to the pump modules or to the programming module. In such embodiments, the programming module may maintain determine, adjust, and/or display values (e.g., default values) of each of the one or more patient parameters for each pump (e.g., pump 22 and pump 26).

Turning now to FIG. 6C, the pump 22 is shown in perspective view with the front door 50 open, showing the upstream fluid line 30 and downstream fluid line 31 in operative engagement with the pump 22. The pump 22 directly acts on a tube 66 (also referred to as a pump segment) that connects the upstream fluid line 30 to the downstream fluid line 31 to form a continuous fluid conduit, extending from the respective fluid supply 38 (FIG. 6A) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 22, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 6C further shows a downstream pressure sensor 82 included in the pump 22 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient (FIG. 6A) and the flow control device, so that the connection of the correct fluid supply with the correct pump may be verified before any fluid is pumped to the patient.

With reference still to FIG. 6C, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 6A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and one or more hardware buttons, a keyboard and/or a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices, hardware buttons, and associated interpretation software, and the like.

Although the disclosure, including the figures, described herein may describe and/or exemplify different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise" and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™ .NET™, C, C++, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system comprising:
   at least one data processor; and
   at least one memory storing instructions which, when executed by the at least one data processor, result in operations comprising:
      receiving, by a mobile infusion pump administration (IPA) device moved adjacent a first data tag coupled to a fluid storage, a fluid delivery protocol, the fluid delivery protocol comprising a fluid parameter associated with a delivery, from a fluid pump, of a fluid from the fluid storage to a patient, wherein the IPA communicates with the first data tag via a single, wireless communication link between the IPA and the first data tag, wherein the single, wireless communication link is the only communication link for all communications between the IPA and the first data tag;
      receiving, by the IPA device moved adjacent a second data tag coupled to a peripheral device, a patient parameter associated with the patient;
      receiving, by the IPA device moved adjacent a third data tag coupled to a peripheral device of a clinician, clinician information including authentication information and clinician parameters, wherein the clinician parameters include at least the clinician's name, a time of a prior scan for the patient, a fluid previously scanned by the clinician, or a count of prior scans for the patient and the type of fluid;
      authenticating, by the IPA device, the clinician using the clinician authentication information;
      upon successful authentication of the clinician, comparing, by the IPA device, the fluid parameter to the patient parameter;
      if the comparison is determined not to be a match, determining that there is an error and outputting an audio alert or visual display alert via the IPA to the authenticated clinician for the clinician to correct the error prior to fluid delivery;
      if the comparison is determined to be a match, configuring, by the IPA device, the fluid pump with the fluid parameter and the patient parameter, thereby causing the fluid pump to display a request to begin delivery of the fluid from the fluid storage to the patient based at least in part on the fluid parameter and the patient parameter and receiving, from the authenticated clinician via a user interface of the IPA device, confirmation to begin fluid delivery of the fluid from the fluid storage to the patient;

causing the fluid pump to deliver the fluid to the patient; and after delivery of the fluid by the fluid pump, updating, by the IPA device, prior infusion information stored on the second data tag of the patient and clinician parameters stored on the third data tag of the clinician, the updating performed by rescanning the second and third data tags and writing the updated patient parameter and associated clinician parameters to the second data tag of the patient and the third data tag of the clinician, wherein the updated patient parameters identify at least one or more of a drug or drugs used in the fluid delivery, a start and end time of the fluid delivery, and a dose of the fluid delivery that includes volume of fluid delivered and frequency of fluid delivery, and wherein the updated clinician parameters identify at least one or more of the clinician's name, a time of a scan for the patient, a fluid scanned by the clinician, a count of scans for the patient, and the type of fluid.

2. The system of claim 1, wherein the comparing further comprises:

determining, by the IPA device, that the patient parameter is not a match with the fluid parameter.

3. The system of claim 1, wherein the receiving the fluid delivery protocol comprises:

scanning, by the IPA device, the first data tag; and storing, by the IPA device, the fluid parameter.

4. The system of claim 1, wherein the fluid parameter comprises one or more of: a start time for delivering the fluid, a volume of the fluid to be delivered, and a frequency for delivering the fluid.

5. The system of claim 1, wherein the receiving the patient parameter comprises:

scanning, by the IPA device, the second data tag; and storing, by the IPA device, the patient parameter.

6. The system of claim 1, wherein the configuring the fluid pump comprises:

scanning, by the IPA device, a fourth data tag coupled to the fluid pump.

7. The system of claim 1, wherein the IPA device comprises a handheld body freestanding from the fluid pump and having a width that fits within a hand of a use.

8. The system of claim 1, further comprising:

the IPA device;

the fluid pump;

the fluid storage; and the peripheral device.

9. The system of claim 1, wherein the single communication link is a direct communication link between the IPA and the first data tag.

10. A computer-implemented method comprising:

receiving, by a mobile infusion pump administration (IPA) device moved adjacent a first data tag coupled to a fluid storage, a fluid delivery protocol, the fluid delivery protocol comprising a fluid parameter associated with a delivery, from a fluid pump, of a fluid from the fluid storage to a patient, wherein the IPA communicates with the first data tag via a single, wireless communication link between the IPA and the first data tag, wherein the single, wireless communication link is the only communication link for all communications between the IPA and the first data tag;

receiving, by the IPA device moved adjacent a second data tag coupled to a peripheral device, a patient parameter associated with the patient;

receiving, by the IPA device moved adjacent a third data tag coupled to a peripheral device of a clinician, clinician information including authentication information and clinician parameters, wherein the clinician parameters include at least the clinician's name, a time of a prior scan for the patient, a fluid previously scanned by the clinician, or a count of prior scans for the patient and the type of fluid;

authenticating, by the IPA device, the clinician using the clinician authentication information;

upon successful authentication of the clinician, comparing, by the IPA device, the fluid parameter to the patient parameter;

if the comparison is determined not to be a match, determining that there is an error and outputting an audio alert or visual display alert via the IPA to the authenticated clinician for the clinician to correct the error prior to fluid delivery;

if the comparison is determined to be a match, configuring, by the IPA device, the fluid pump with the fluid parameter and the patient parameter, thereby causing the fluid pump to display a request to begin delivery of the fluid from the fluid storage to the patient based at least in part on the fluid parameter and the patient parameter and receiving, from the authenticated clinician via a user interface of the IPA device, confirmation to begin fluid delivery of the fluid from the fluid storage to the patient;

causing the fluid pump to deliver the fluid to the patient; and after delivery of the fluid by the fluid pump, updating, by the IPA device, prior infusion information stored on the second data tag of the patient and clinician parameters stored on the third data tag of the clinician, the updating performed by rescanning the second and third data tags and writing the updated patient parameter and associated clinician parameters to the second data tag of the patient and the third data tag of the clinician, wherein the updated patient parameters identify at least one or more of a drug or drugs used in the fluid delivery, a start and end time of the fluid delivery, and a dose of the fluid delivery that includes volume of fluid delivered and frequency of fluid delivery, and wherein the updated clinician parameters identify at least one or more of the clinician's name, a time of a scan for the patient, a fluid scanned by the clinician, a count of scans for the patient, and the type of fluid.

11. The method of claim 10, wherein the comparing further comprises:

determining, by the IPA device, that the patient parameter is not the same as the fluid parameter.

12. The method of claim 10, wherein the receiving the fluid delivery protocol comprises:

scanning, by the IPA device, the first data tag; and storing, by the IPA device, the fluid parameter.

13. The method of claim 10, wherein the fluid parameter comprises one or more of: a fluid type, a rate of fluid delivery, a start time for delivering the fluid, a volume of the fluid to be delivered, a frequency for delivering the fluid, a name of the patient, and a patient ID.

14. The method of claim 10, wherein the receiving patient parameter comprises:

scanning, by the IPA device, the second data tag; and storing, by the IPA device, the patient parameter.

15. The method of claim 10, wherein the configuring the fluid pump comprises:

scanning, by the IPA device, a fourth data tag coupled to the fluid pump.

16. A non-transitory computer-readable storage medium including program code, which when executed by at least one data processor, cause operations comprising:

receiving, by a mobile infusion pump administration (IPA) device moved adjacent a first data tag coupled to a fluid storage, a fluid delivery protocol, the fluid delivery protocol comprising a fluid parameter associated with a delivery, from a fluid pump, of a fluid from the fluid storage to a patient, wherein the IPA communicates with the first data tag via a single, wireless communication link between the IPA and the first data tag, wherein the single, wireless communication link is the only communication link for all communications between the IPA and the first data tag;

receiving, by the IPA device moved adjacent a second data tag coupled to a peripheral device, a patient parameter associated with the patient;

receiving, by the IPA device moved adjacent a third data tag coupled to a peripheral device of a clinician, clinician information including authentication information and clinician parameters, wherein the clinician parameters include at least the clinician's name, a time of a prior scan for the patient, a fluid previously scanned by the clinician, or a count of prior scans for the patient and the type of fluid;

authenticating, by the IPA device, the clinician using clinician authentication information;

upon successful authentication of the clinician, comparing, by the IPA device, the fluid parameter to the patient parameter;

if the comparison is determined not to be a match, determining that there is an error and outputting an audio alert or visual display alert via the IPA to the authenticated clinician for the clinician to correct the error prior to fluid delivery;

if the comparison is determined to be a match, configuring, by the IPA device, the fluid pump with the fluid parameter and the patient parameter, thereby causing the fluid pump to display a request to begin delivery of the fluid from the fluid storage to the patient based at least in part on the fluid parameter and the patient parameter and receiving, from the authenticated clinician via a user interface of the IPA device, confirmation to begin fluid delivery of the fluid from the fluid storage to the patient;

causing the fluid pump to deliver the fluid to the patient; and after delivery of the fluid by the fluid pump, updating, by the IPA device, prior infusion information stored on the second data tag of the patient and clinician parameters stored on the third data tag of the clinician, the updating performed by rescanning the second and third data tags and writing the updated patient parameter and associated clinician parameters to the second data tag of the patient and the third data tag of the clinician, wherein the updated patient parameters identify at least one or more of a drug or drugs used in the fluid delivery, a start and end time of the fluid delivery, and a dose of the fluid delivery that includes volume of fluid delivered and frequency of fluid delivery, and wherein the updated clinician parameters identify at least one or more of the clinician's name, a time of a scan for the patient, a fluid scanned by the clinician, a count of scans for the patient, and the type of fluid.

* * * * *